United States Patent
Larsen et al.

(12) 
(10) Patent No.: US 6,251,895 B1
(45) Date of Patent: *Jun. 26, 2001

(54) OLANZAPINE DIHYDRATE D

(75) Inventors: Samuel Dean Larsen, West Lafayette, IN (US); John Richard Nichols, Merscyside (GB); Susan Marie Reutzel, Indianapolis; Gregory Alan Stephenson, Fishers, both of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,883

(22) Filed: Sep. 23, 1997

Related U.S. Application Data

(60) Provisional application No. 60/026,486, filed on Sep. 23, 1996.

(51) Int. Cl.$^7$ .......................... A61K 31/44; C07D 243/10
(52) U.S. Cl. ............................................. 514/220; 540/557
(58) Field of Search ............................ 424/464; 514/220; 540/557

(56) References Cited

U.S. PATENT DOCUMENTS

| | | | |
|---|---|---|---|
| 5,229,382 | 7/1993 | Chakrabarti et al. | 514/220 |
| 5,302,716 | * 4/1994 | Berger et al. | 540/519 |
| 5,631,250 | 5/1997 | Bunnell et al. | 514/220 |
| 5,736,541 | * 4/1998 | Bunnell et al. | 514/220 |

FOREIGN PATENT DOCUMENTS

| | | | |
|---|---|---|---|
| 0 454 436 | 10/1991 | (EP) | C07D/495/04 |
| 0 582 368 | 2/1994 | (EP) | C07D/495/04 |
| 0 733 368 | 9/1996 | (EP) | A61K/31/55 |
| 0 733 634 | 9/1996 | (EP) | C07D/495/04 |
| 0 766 635 | 9/1996 | (EP) | C07D/495/04 |

* cited by examiner

*Primary Examiner*—Edward J. Webman
(74) *Attorney, Agent, or Firm*—Arleen Palmberg; MaCharri Vorndran-Jones; Nancy J. Harrison

(57) ABSTRACT

The present invention provides the novel Dihydrate D 2-methyl-thieno-benzodiazepine and a formulation therefor.

21 Claims, No Drawings

OLANZAPINE DIHYDRATE D

CROSS REFERENCE TO RELATED APPLICATION

This application claims the benefit of U.S. Provisional Application No. 60/026,486, filed Sept. 23, 1996.

FIELD OF THE INVENTION

This invention relates to the crystalline dihydrate D of 2-methyl-4-(4-methyl-1-piperazinyl)-10H-thieno[2,3-b][1,5]benzodiazepine (referred to herein as "olanzapine"). The invention more specifically relates to a novel crystalline form which is particularly useful for preparing an aqueous olanzapine formulation.

BACKGROUND OF THE INVENTION

The stable crystalline Dihydrate D is particularly important for the commercial development of new formulations of the pharmaceutically active olanzapine. Olanzapine is useful for treating psychotic patients. Often an aqueous formulation or a formulation that is prepared using aqueous mixing is desired. Applicants have discovered that Form II olanzapine is the most stable anhydrous form of olanzapine, providing a stable anhydrous formulation with pharmaceutically desired characteristics. However, a stable dihydrate was desired to provide pharmaceutically elegant aqueous formulations.

A novel dihydrate crystal form of olanzapine has now been synthesized and characterized which possesses distinct advantages over the previously known forms, that is the material produced using the methods described in U.S. Pat. No. 5,299,382 (hereinafter referred to as "the '382 patent"), when aqueous formulations or a stable aqueous intermediate is desired. This novel dihydrate crystal form is clearly distinguishable therefrom by x-ray powder diffractometry. U.S. Pat. No. 5,229,382 is hereby incorporated by reference in its entirety.

Applicants have discovered that Dihydrate D olanzapine is essential to assure a pharmaceutically elegant, aqueous formulation. Applicants have found that olanzapine forms a Dihydrate B; however, this form appears to be quite unstable compared to Dihydrate D. Dihydrate D requires controlled conditions to prepare the substantially pure Dihydrate D material; however, once prepared, the Dihydrate D is surprisingly robust and stable. Therefore, Dihydrate D olanzapine is most desired and appears to be essential for use in preparing consistently stable commercial pharmaceutically elegant aqueous olanzapine formulations as well as for pharmaceutically elegant formulations prepared using extensive aqueous mixing.

SUMMARY OF THE INVENTION

The presently claimed invention provides the stable crystalline Dihydrate D olanzapine polymorph (herein referred to as "Dihydrate D") having a typical x-ray powder diffraction pattern as represented by the following interplanar spacings (d) as set forth in Table 1:

TABLE 1

| d |
|---|
| 9.4511 |
| 7.7098 |

TABLE 1-continued

| d |
|---|
| 7.4482 |
| 6.9807 |
| 6.5252 |
| 5.7076 |
| 5.5539 |
| 5.223 |
| 4.9803 |
| 4.8908 |
| 4.784 |
| 4.6947 |
| 4.4271 |
| 4.3956 |
| 4.3492 |
| 4.2834 |
| 4.1156 |
| 3.7837 |
| 3.7118 |
| 3.5757 |
| 3.482 |
| 3.3758 |
| 3.3274 |
| 3.2413 |
| 3.1879 |
| 3.135 |
| 3.0979 |
| 3.016 |
| 2.9637 |
| 2.907 |
| 2.8256 |
| 2.7914 |
| 2.7317 |
| 2.6732 |
| 2.5863 |

The x-ray powder diffraction patterns set forth herein were obtained with a copper k of wavelength=1.541 Å. The interplanar spacings in the column marked "d" are reported in Angstroms. The detector was a Kevex silicon lithium solid state detector.

The present invention further provides an aqueous formulation comprising Dihydrate D as an active ingredient with one or more carriers or diluents therefor.

DETAILED DESCRIPTION OF THE INVENTION

Applicants have discovered that 2-methyl-4-(4-methyl-1-piperazinyl)-10H-thieno[2,3-b][(1,5]benzodiazepine, which is a compound of Formula (I):

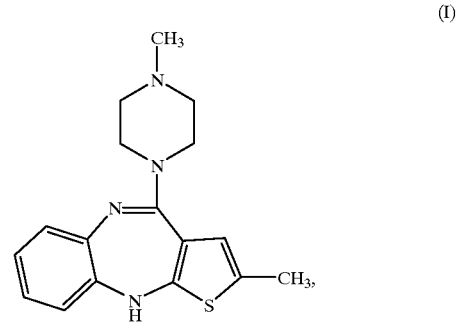

exists as two different dihydrate forms which are distinguishable by x-ray powder diffractometry. The less stable, and therefore less desired dihydrate has been designated as Dihydrate B. Applicants have discovered that a stable dehydrate is necessary for the preparation of a consistently stable pharmaceutically elegant aqueous formulation. Both dihydrate forms are clearly distinguishable from the polymorph taught in the '382 patent.

The polymorph obtainable by the process taught in the '382 patent is an anhydrate form which is not as stable as desired and not well suited for pharmaceutical formulations. The anhydrate obtainable by the process of the '382 patent will be designated as Form I and has a typical x-ray powder diffraction pattern substantially as follows, obtained using a Siemens D5000 x-ray powder diffractometer, wherein d represents the interplanar spacing:

| d |
| --- |
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows, wherein d represents the interplanar spacing and $I/I_1$ represents the typical relative intensities:

| d | $I/I_1$ |
| --- | --- |
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |

-continued

| d | $I/I_1$ |
| --- | --- |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_\alpha$ of wavelength $\lambda=1.541$ Å. The interplanar spacings in the column marked "d" are in Angstroms. The typical relative intensities are in the column marked "$I/I_1$".

A typical example of an x-ray diffraction pattern for the anhydrous Form II polymorph (see EP 733,635) is as follows wherein d represents the interplanar spacing and $I/I_1$ represents the typical relative intensities:

| d | $I/I_i$ |
| --- | --- |
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

As used herein "substantially pure" refers to Dihydrate D associated with less than about 20% Dihydrate B, preferably less than about 5% Dihydrate B and may preferably be less than about 2% Dihydrate B. Further, "substantially pure" Dihydrate D will contain less than about 0.5% related substances, wherein "related substances" refers to undesired chemical impurities or residual organic solvent.

Advantageously, the novel polymorph of the invention will be free from chemical solvates, for instance existing as the substantially pure Dihydrate D.

Pharmaceutical formulations containing Dihydrate D should contain less than about 20% Dihydrate B, more preferably less than about 10% Dihydrate B polymorph.

Olanzapine has useful central nervous system activity. This activity has been demonstrated using well-established procedures, for example, as described in the '382 patent. Dihydrate D provided by the present invention appears to have the same profile of receptor activity and has the same therapeutic uses as olanzapine described in the '382 patent. Therefore, Dihydrate D is useful for the treatment of schizophrenia, schizophreniform disorders, psychosis, mild anxiety states, and functional bowel disorders.

Dihydrate D is effective over a wide dosage range, the actual dose administered being dependent on the condition being treated. For example, in the treatment of adult humans, dosages of from about 0.25 to 50 mg, preferably from 1 to 30 mg, and most preferably 1 to 25 mg per day may be used. A once a day dosage is normally sufficient, although divided doses may be administered. For treatment of central nervous system disorders, a dose range of from 1 to 30 mg, preferably 2.5 to 20 mg per day is suitable.

A typical example of an x-ray diffraction pattern for Dihydrate D is as follows, wherein d represents the interplanar spacing and $I/I_1$ represents the typical relative intensities:

| d | $I/I_1$ |
|---|---|
| 9.4511 | 100.00 |
| 7.7098 | 14.23 |
| 7.4482 | 22.43 |
| 6.9807 | 5.73 |
| 6.5252 | 5.45 |
| 5.7076 | 4.24 |
| 5.5539 | 1.60 |
| 5.223 | 62.98 |
| 4.9803 | 22.21 |
| 4.8908 | 15.03 |
| 4.784 | 27.81 |
| 4.6947 | 5.15 |
| 4.4271 | 13.00 |
| 4.3956 | 16.63 |
| 4.3492 | 34.43 |
| 4.2834 | 51.38 |
| 4.1156 | 18.32 |
| 3.7837 | 5.30 |
| 3.7118 | 1.56 |
| 3.5757 | 0.71 |
| 3.482 | 9.39 |
| 3.3758 | 24.87 |
| 3.3274 | 13.49 |
| 3.2413 | 5.97 |
| 3.1879 | 1.04 |
| 3.135 | 3.18 |
| 3.0979 | 1.43 |
| 3.016 | 1.95 |
| 2.9637 | 0.48 |
| 2.907 | 2.42 |
| 2.8256 | 7.46 |
| 2.7914 | 3.61 |
| 2.7317 | 1.47 |
| 2.6732 | 5.19 |
| 2.5863 | 10.62 |

The x-ray powder diffraction patterns herein were obtained with a copper $K_\alpha$ of wavelength $\lambda=1.541$ Å. The interplanar spacings in the column marked "d" are in Angstroms. The typical relative intensities are in the column marked "$I/I_1$".

The typical example of an x-ray diffraction pattern for the less stable Dihydrate B polymorph is as follows, wherein d represents the interplanar spacing and $I/I_1$ represents the typical relative intensities:

| d | $I/I_1$ |
|---|---|
| 9.9045 | 100.00 |
| 6.9985 | 0.39 |
| 6.763 | 0.17 |
| 6.4079 | 0.13 |
| 6.1548 | 0.85 |
| 6.0611 | 0.99 |
| 5.8933 | 0.35 |
| 5.6987 | 0.12 |
| 5.4395 | 1.30 |
| 5.1983 | 0.67 |
| 5.0843 | 0.24 |
| 4.9478 | 0.34 |
| 4.7941 | 6.53 |
| 4.696 | 1.26 |
| 4.5272 | 2.65 |
| 4.4351 | 2.18 |
| 4.3474 | 1.85 |
| 4.2657 | 0.49 |
| 4.1954 | 0.69 |
| 4.0555 | 0.42 |
| 3.9903 | 0.89 |
| 3.9244 | 1.52 |
| 3.8561 | 0.99 |
| 3.8137 | 1.44 |
| 3.7671 | 0.92 |
| 3.6989 | 1.78 |
| 3.6527 | 0.60 |
| 3.5665 | 0.34 |
| 3.4879 | 1.41 |
| 3.3911 | 0.27 |
| 3.3289 | 0.20 |
| 3.2316 | 0.31 |
| 3.1982 | 0.19 |
| 3.1393 | 0.35 |
| 3.0824 | 0.18 |
| 2.9899 | 0.26 |
| 2.9484 | 0.38 |
| 2.9081 | 0.29 |
| 2.8551 | 0.37 |
| 2.8324 | 0.49 |
| 2.751 | 0.37 |
| 2.7323 | 0.64 |
| 2.6787 | 0.23 |
| 2.6424 | 0.38 |
| 2.5937 | 0.21 |

A typical example of an x-ray diffraction pattern for the anhydrous Form II polymorph is as follows, wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |

-continued

| d | I/I₁ |
|---|---|
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

The compounds and processes of the present invention are useful for preparing compounds having beneficial central nervous system activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some preferred characteristics of this invention include the following:

A) A compound which is the Dihydrate D polymorph of 2-methyl-4-(4-methyl-1-piperazinyl)-10H-thieno[2,3-b][1,5]benzodiazepine (Dihydrate D polymorph);

B) A compound which is the substantially pure Dihydrate D polymorph;

C) An aqueous suspension formulation containing Dihydrate D;

D) A tablet formulation containing substantially pure Dihydrate D which is packaged in a blister packaged under humid conditions;

E) A consistently stable pharmaceutically elegant aqueous formulation containing substantially pure Dihydrate D;

F) Substantially pure Dihydrate D is formulated in a unit dosage form;

G) Substantially pure Dihydrate D is formulated for rapid dissolution;

H) Substantially pure Dihydrate D is used for treating a condition selected from the group consisting of a psychosis, schizophrenia, a schizophreniform disorder, mild anxiety, and acute mania;

I) An aqueous suspension formulation containing Dihydrate D as an active ingredient wherein such formulation is suitable for injection.

J) A tablet formulation containing substantially pure Dihydrate D which is package in an air resistant package.

Depending on the method of administration, the compositions for the treatment of central nervous system conditions may be formulated as tablets, capsules, gel or suspension for transdermal delivery, suspensions or elixirs for oral use or suppositories. If such formulation is a tablet or capsule, then such formulation is most preferably packaged under humid conditions and sealed in an air impermeable sachet or blister pack. Preferably, the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is an aqueous suspension comprising 0.25 to 75 mg or 1 to 30 mg of active ingredient together with a pharmaceutically acceptable carrier therefor.

The starting materials for the present invention can be prepared by a variety of procedures well known to those of ordinary skill in the art. The material to be employed as starting materials in the process of this invention can be prepared by the general procedure taught by Chakrabarti in U.S. Pat. No. 5,229,382 ('382), herein incorporated by reference in its entirety.

The Dihydrate D is prepared by extensive stirring of technical olanzapine, which may be prepared as described by Preparation 1, under aqueous conditions. The term "aqueous conditions" refers to an aqueous solvent which may be either water or a solvent mixture comprising water and an organic solvent which is sufficiently water miscible to allow the required stoichiometric quantity of water to be present in the solvent mixture. If a solvent mixture is utilized, then the organic solvent must be removed, leaving behind the water, and/or replaced with water. The term "extensive stirring" shall be from about one (1) hour to about six (6) days; however, the artisan will appreciate that the time will vary with the reaction conditions such as temperature, pressure, and solvent. It maybe preferred to stir for at least about four (4) hours. It is preferred that the aqueous conditions include an aqueous solvent. However, it is to be noted that to form polymorph D, rather than other dihydrate polymorphs, more extensive stirring and/or agitation is required, preferably is excess of 12 hours, more preferably in excess of 24 hours. Further, a wetting agent may be added to the aqueous mixture to speed up the formation of the stable Dihydrate D.

Dihydrate D may be air dried or dried using other standard techniques which are sufficiently mild to avoid desolvation of the Dihydrate D.

The completion of the reaction may be monitored using x-ray powder diffraction and other such methods familiar to the skilled artisan. Several such techniques are described below.

Compound characterization methods include, for example, x-ray powder pattern analysis, thermogravimetric analysis (TGA), differential scanning calorimetery (DSC), titrametric analysis for water, and $H^1$-NMR analysis for solvent content.

Accordingly, pharmaceutical compositions comprising Dihydrate D, as active ingredient associated with a pharmaceutically acceptable carrier may be prepared. In making the compositions of the invention conventional techniques for the preparation of pharmaceutical compositions can be used. For example, the active ingredient can usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be absorbed in a granular solid container, for example, in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, if desired, be formulated so as to provide quick, sustained or delayed release of the active ingredient after administration to the patient. For example, one such quick release formulation is described in U.S. Pat. Nos. 4,305,502 and 4,371,516, hereby incorporated by reference.

It is typically preferred that such formulation includes a pharmaceutically acceptable flavoring agent or combinations of such agents, including natural and synthetic flavoring agents such as aspartame and flavor enhancing agents, such as the commercial product VELTOL® (Pfizer); preservatives such as methyl paraben, propyl paraben and combinations thereof are further preferred.

Another preferred embodiment of this invention is the formulation methods described in U.S. Pat. No. 4,758,598, herein incorporated by reference in its entirety.

A particularly preferred method for treating a subject suffering from or susceptible to a psychotic condition comprises administering an aqueous oral suspension formulation comprising Dihydrate D olanzapine and pharmaceutically acceptable carriers and/or excipients.

The following examples are provided for purposes of illustration and are not to be construed as limiting the scope of the claimed invention.

PREPARATION 1

Technical Grade Olanzapine

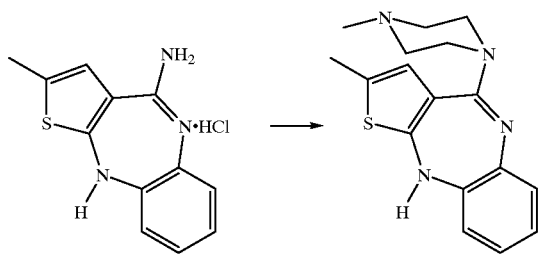

Intermediate 1

In a suitable three neck flask the following was added:
Dimethylsulfoxide (analytical): 6 volumes
Intermediate 1:75 g
N-Methylpiperazine (reagent): 6 equivalents Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until ≦5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water were added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

EXAMPLE 1

Dihydrate D

A 100 g sample of technical grade olanzapine (see Preparation 1) was suspended in water (500 mL). The mixture was stirred at about 25° C. for about 5 days. The product was isolated using vacuum filtration. The product was identified as Dihydrate D olanzapine using x-ray powder analysis. Yield: 100 g. TGA mass loss was 10.2%.

EXAMPLE 2

A sample of gelatin powder (1 g) is admixed with maltodextran (2 g), gelatin A (0.5 g); sucrose (2 g) and aspartame (1 g). Distilled water is added to the mixture to about 100 mL total volume. The mixture is stirred and heated to about 60° C. The mixture should be heated until it appears to be a clear solution. The mixture is cooled to about 37° C. Blister molds are prepared by rinsing with a solution of lecithein (about 10%) in about 190 proof grain alcohol. The molds so prepared are dried at room temperature. An aliquot of the cooled mixture is added to each compartment of the mold. The mold containing the mixture is cooled to a temperature of about −10° C. or lower for about 40 minutes. The mold containing the mixture is removed from the <−10° C. environment and about 20 mg of anhydrous olanzapine is added to the surface of each tablet within the mold. The mold should remain protected from thawing. The mold containing the mixture and olanzapine is again cooled to about −10° C. for about 40 minutes.

The mold is removed from the cooled about −10° C. environment and an additional aliquot of the gelatin based mixture (to which no olanzapine has been added) is added to the surface of each compartment of the mold prepared as described supra. The mold is again cooled to about −10° C. for about 40 minutes.

The tablets are removed from the mold to a mesh plastic bag. The bag and its contents are hermetically sealed in a container of anhydrous ethyl alcohol and maintained at a temperature of −20° C. The tablets are maintained in the hermetically sealed bag until the tablets are completely dehydrated. The dehydration continues until no odor or other evidence of alcohol can be detected on the tablets. The formulation is studied using x-ray powder diffraction techniques to assure that substantially pure Dihydrate D is present.

EXAMPLE 3

Suspensions each containing 5 mg of medicament per 5 ml dose are as follows:

|  | Per 5 ml of suspension |
|---|---|
| Dihydrate D | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the past with stirring. Sufficient water is then added to produce the required volume.

EXAMPLE 4

Suspensions each containing 20 mg of medicament per 5 ml dose are as follows:

|  | Per 5 ml of suspension |
|---|---|
| Dihydrate D | 20 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

We claim:

1. Olanzapine dihydrate D, which has an X-ray powder diffraction pattern with the following interplanar spacings (d) in Angstroms:

| d |
|---|
| 9.4511 |
| 7.7098 |
| 7.4482 |
| 6.9807 |
| 6.5252 |
| 5.7076 |
| 5.5539 |
| 5.223 |
| 4.9803 |
| 4.8908 |
| 4.784 |
| 4.6947 |
| 4.4271 |
| 4.3956 |
| 4.3492 |
| 4.2834 |
| 4.1156 |
| 3.7837 |
| 3.7118 |
| 3.5757 |
| 3.482 |
| 3.3758 |
| 3.3274 |
| 3.2413 |
| 3.1879 |
| 3.135 |
| 3.0979 |
| 3.016 |
| 2.9637 |
| 2.907 |
| 2.8256 |
| 2.7914 |
| 2.7317 |
| 2.6732 |
| 2.5863 |

2. Olanzapine dihydrate D as claimed in claim 1 wherein the interplanar spacings have the following relative intensities ($I/I_1$)

| d | $I/I_1$ |
|---|---|
| 9.4511 | 100.00 |
| 7.7098 | 14.23 |
| 7.4482 | 22.43 |
| 6.9807 | 5.73 |
| 6.5252 | 5.45 |
| 5.7076 | 4.24 |
| 5.5539 | 1.60 |
| 5.223 | 62.98 |
| 4.9803 | 22.21 |
| 4.8908 | 15.03 |
| 4.784 | 27.81 |
| 4.6947 | 5.15 |
| 4.4271 | 13.00 |
| 4.3956 | 16.63 |
| 4.3492 | 34.43 |
| 4.2834 | 51.38 |
| 4.1156 | 18.32 |
| 3.7837 | 5.30 |
| 3.7118 | 1.56 |
| 3.5757 | 0.71 |
| 3.482 | 9.39 |
| 3.3758 | 24.87 |
| 3.3274 | 13.49 |
| 3.2413 | 5.97 |
| 3.1879 | 1.04 |
| 3.135 | 3.18 |
| 3.0979 | 1.43 |
| 3.016 | 1.95 |
| 2.9637 | 0.48 |
| 2.907 | 2.42 |
| 2.8256 | 7.46 |
| 2.7914 | 3.61 |
| 2.7317 | 1.47 |
| 2.6732 | 5.19 |
| 2.5863 | 10.62 |

3. Olanzapine dihydrate D of claim 1 in substantially pure form.

4. Olanzapine dihydrate D of claim 2 in substantially pure form.

5. Olanzapine dihydrate D of claim 4 which contains less than 2% olanzapine dihydrate B.

6. A pharmaceutical formulation comprising as an active ingredient olanzapine dihydrate D of claim 1 and a pharmaceutically acceptable carrier, diluent, or excipient.

7. A pharmaceutical formulation comprising as an active ingredient olanzapine dihydrate D of claim 2 and a pharmaceutically acceptable carrier, diluent, or excipient.

8. A pharmaceutical formulation comprising as an active ingredient olanzapine dihydrate D of claim 3 and a pharmaceutically acceptable carrier, diluent, or excipient.

9. A formulation of claim 6 wherein the formulation is an aqueous suspension.

10. A formulation of claim 6 wherein the formulation is a tablet.

11. A formulation of claim 8 wherein the formulation is an aqueous suspension.

12. A method for treating a psychotic condition in a mammal comprising administering an effective amount of olanzapine dihydrate D of claim 1 to the mammal.

13. A method for treating a condition selected from the group consisting of anxiety, schizophrenia, schizophreniform disorder, a functional bowel disorder, and psychosis in a mammal, comprising administering an effective amount of olanzapine dihydrate D of claim 1 to the mammal.

14. A process for preparing a crystalline olanzapine dihydrate D comprising stirring technical grade olanzapine in an aqueous solvent from about one hour to about six days until dihydrate D is formed.

15. The process of claim 14 wherein the olanzapine is stirred for at least 12 hours.

16. The process of claim 15 wherein the olanzapine is stirred for at least 24 hours.

17. The process of claim 16 wherein the olanzapine is stirred for about 5 days.

18. The process of claim 14 wherein the solvent includes a wetting agent.

19. The process of claim 14 which includes the additional step of drying the dihydrate D using a technique sufficiently mild to avoid desolvation of the dihydrate D.

20. Olanzapine dihydrate D having an X-ray powder diffraction pattern with the following interplanar spacings (d) in Angstroms:

9.45, 7.45, 5.22, 4.40, 4.35 & 4.28.

21. Olanzapine dihydrate D having an X-ray powder diffraction pattern with the following interplanar spacings (d) in Angstroms: 9.45, 7.71, 7.45, 5.22, 4.98, 4.78, 4.40, 4.35, 4.28 & 3.38.

* * * * *